(12) United States Patent
Bratkovski et al.

(10) Patent No.: US 7,245,370 B2
(45) Date of Patent: Jul. 17, 2007

(54) NANOWIRES FOR SURFACE-ENHANCED RAMAN SCATTERING MOLECULAR SENSORS

(75) Inventors: Alexandre Bratkovski, Mountain View, CA (US); M. Saif Islam, Sacramento, CA (US); Theodore I. Kamins, Palo Alto, CA (US); Zhiyong Li, Palo Alto, CA (US); Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 194 days.

(21) Appl. No.: 11/030,733

(22) Filed: Jan. 6, 2005

(65) Prior Publication Data

US 2006/0146323 A1    Jul. 6, 2006

(51) Int. Cl.
*G01J 3/44*       (2006.01)
*G01N 21/65*      (2006.01)

(52) U.S. Cl. .................................... 356/301

(58) Field of Classification Search ............. 356/301
See application file for complete search history.

(56) References Cited

U.S. PATENT DOCUMENTS

| | | |
|---|---|---|
| 4,674,878 A | 6/1987 | Vo-Dinh |
| 4,944,985 A | 7/1990 | Alexander et al. |
| 5,017,007 A | 5/1991 | Milne et al. |
| 5,242,828 A | 9/1993 | Bergstrom et al. |
| 5,255,067 A | 10/1993 | Carrabba et al. |
| 5,527,712 A | 6/1996 | Sheehy |
| 5,609,907 A | 3/1997 | Natan |
| 5,772,905 A | 6/1998 | Chou |
| 5,837,552 A | 11/1998 | Cotton et al. |
| 6,149,868 A | 11/2000 | Natan et al. |
| 6,165,911 A | 12/2000 | Calveley |
| 6,248,674 B1 | 6/2001 | Kamins et al. |
| 6,365,059 B1 | 4/2002 | Pechenik |
| 6,406,777 B1 | 6/2002 | Boss et al. |
| 6,432,740 B1 | 8/2002 | Chen |
| 6,579,721 B1 | 6/2003 | Natan et al. |
| 6,623,977 B1 | 9/2003 | Farquharson et al. |
| 6,649,683 B2 | 11/2003 | Bell |
| 6,743,368 B2 | 6/2004 | Lee |
| 6,773,616 B1 | 8/2004 | Chen et al. |
| 2002/0142480 A1 | 10/2002 | Natan |
| 2003/0120137 A1 | 6/2003 | Pawluczyk |
| 2003/0231304 A1 | 12/2003 | Chan et al. |
| 2004/0135997 A1 | 7/2004 | Chan et al. |
| 2006/0038990 A1* | 2/2006 | Habib et al. ............. 356/301 |
| 2006/0054881 A1* | 3/2006 | Li et al. ..................... 257/19 |

OTHER PUBLICATIONS

Drew, Christopher, et al., "Metal Oxide-Coated Polymer Nanofibers," Nano Lett., vol. 3, No. 2, 2003, pp. 143-147.

(Continued)

*Primary Examiner*—F. L. Evans

(57) ABSTRACT

A SERS-active structure is disclosed that includes a substrate and at least two nanowires disposed on the substrate. Each of the at least two nanowires has a first end and a second end, the first end being attached to the substrate and the second end having a SERS-active tip. A SERS system is also disclosed that includes a SERS-active structure. Also disclosed are methods for forming a SERS-active structure and methods for performing SERS with SERS-active structures.

42 Claims, 10 Drawing Sheets

OTHER PUBLICATIONS

Emory, Steven R., et al., "Screening and Enrichment of Metal Nanoparticles with Novel Optical Properties," J. Phys. Chem. B, vol. 102, No. 3, 1998, pp. 493-497.

Green, Mino, et al., "SERS Substrates Fabricated by Island Lithography: The Silver/Pyridine System," J. Phys. Chem. B, vol. 107, No. 47, 2003, pp. 13015-13021.

Kamins, T.I., et al., "Chemically vapor deposited Si nanowires nucleated by self-assembled Ti islands on patterned and unpatterned Si substrates," Physica E 13, 2002, pp. 995-998.

Kamins, T.I., et al., "Growth and Structure of Chemically Vapor Deposited Ge Nanowires on Si Substrates," Nano Lett., vol. 4, No. 3, 2004, pp. 503-506.

Kneipp, Katrin, et al., "Single Molecular Detection Using Surface-Enhanced Raman Scattering (SERS)," Physical Review Letters, vol. 78, No. 9, Mar. 3, 1997, pp. 1667-1670.

Kottmann, Jorg P., et al., "Plasmon resonances of silver nanowires with a nonregular cross section," Physical Review B, vol. 64, 235402-1 through 10, 2001.

Liu, Feng-Ming, et al., "Efficient SERS substrates made by electroless silver deposition into patterned silicon structures," J. Mater. Chem., vol. 14, 2004, pp. 1526-1532.

Michaels, Amy M., et al., "Surface Enhanced Raman Spectroscopy of Individual Rhodamine 6G Molecules on Large Ag Nanocrystals," J. Am. Chem. Soc., vol. 121, No. 43, 1999, pp. 9932-9939.

Pinto, N.J., et al., "Electroless Deposition of Thin Metallic Films on Polymer Fibers Prepared via Electrospinning," Polymer Preprints 2003, 44(2), pp. 138-139.

Tao, Andrea, et al., "Langmuir-Blodgett Silver Nanowire Monolayers for Molecular Sensing Using Surface-Enhanced Raman Spectroscopy," Nano Lett., vol. 3, No. 9, 2003, pp. 1229-1233.

* cited by examiner

▼ = ANTIGEN
Y = ANTIBODY

NANOWIRES FOR SURFACE-ENHANCED RAMAN SCATTERING MOLECULAR SENSORS

FIELD OF THE INVENTION

The present invention relates to surface enhanced Raman spectroscopy (SERS). More particularly, the invention relates to SERS-active structures for use in molecular sensors that include nanowires having SERS-active tips, methods for forming SERS-active structures, and methods for performing SERS using SERS-active structures.

BACKGROUND OF THE INVENTION

Raman spectroscopy is a well-known technique for performing chemical analysis. In conventional Raman spectroscopy, high intensity monochromatic light provided by a light source, such as a laser, is directed onto an analyte (or sample) that is to be chemically analyzed. A majority of the incident photons are elastically scattered by the analyte molecule. In other words, the scattered photons have the same energy, and thus the same frequency, as the photons that were incident on the analyte. However, a small fraction of the photons (i.e., about 1 in $10^7$ photons) are inelastically scattered by the analyte molecules. These inelastically scattered photons have a different frequency than the incident photons. This inelastic scattering of photons is termed the "Raman effect." The inelastically scattered photons may have frequencies greater than, or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the frequency of the inelastically scattered Raman photons against the intensity thereof. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the weak Raman signal for detection. Surface enhanced Raman spectroscopy (SERS) is a technique that allows for generation of a stronger Raman signal from an analyte relative to conventional Raman spectroscopy for a sample with the same number of analyzed molecules. In SERS, the analyte molecules are adsorbed onto, or placed adjacent to, an activated metal surface or structure (a "SERS-active structure"). The interactions between the molecules and the surface cause an increase in the strength of the Raman signal. The mechanism of Raman signal enhancement exhibited in SERS is not completely understood. Two main theories of enhancement mechanisms have been presented in the literature: electromagnetic enhancement and chemical (or "first layer") enhancement. (For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," *J. Am. Chem. Soc.* 121, 9932-39 (1999)).

Several SERS-active structures have been employed in SERS techniques, including activated electrodes in electrolytic cells, activated metal colloid solutions, and activated metal substrates such as a roughened metal surface or metal "islands" formed on a substrate. For example, it has been shown that adsorbing analyte molecules onto or near a specially roughened metal surface made from silver or gold may enhance the Raman scattering intensity by factors of between $10^3$ and $10^6$.

Recently, SERS has been performed employing randomly oriented nanometer scale needles, particles, and wires, as opposed to a simple roughened metallic surface. The intensity of the Raman scattered photons from a molecule adsorbed on such a metal surface may be increased by factors as high as $10^{16}$. At this level of sensitivity, SERS has been used to detect single molecules. Detecting single molecules with high sensitivity and molecular specificity is of great interest in the fields of chemistry, biology, medicine, pharmacology, and environmental science.

Accordingly, there is a need for highly-sensitive SERS-active structures that can be used in molecular sensors.

BRIEF SUMMARY OF THE INVENTION

The present invention relates to surface enhanced Raman spectroscopy (SERS). More particularly, the invention relates to SERS-active structures for use in molecular sensors that include nanowires having SERS-active tips, methods for forming SERS-active structures, and methods for performing SERS using SERS-active structures.

A SERS-active structure for use in a sensor for an analyte molecule is described that includes a substrate and at least two nanowires. Each of the at least two nanowires has a first end and a second end, the first end being attached to the substrate and the second end including a SERS-active tip. The SERS-active structure includes a ligand to the analyte molecule attached to the SERS-active structure for holding the analyte molecule in proximity to the SERS-active tips of the at least two nanowires.

A SERS system operable as a sensor for an analyte molecule is described that includes a SERS-active structure, an excitation radiation source configured to irradiate the SERS-active structure, and a detector configured to receive Raman-scattered radiation scattered by an analyte molecule located adjacent the SERS-active structure. The SERS-active structure includes a substrate and at least two nanowires. Each of the at least two nanowires has a first end and a second end, the first end being attached to the substrate and the second end including a SERS-active tip. The SERS-active structure includes a ligand to the analyte molecule attached to the SERS-active structure for holding the analyte molecule in proximity to the SERS-active tips of the at least two nanowires.

A method for detecting an analyte molecule is disclosed that includes the steps of providing a SERS-active structure, placing the SERS-active structure in an environment in which it is desired to detect the analyte molecule, irradiating the SERS-active structure with excitation radiation, and detecting Raman-scattered radiation. The SERS-active structure includes a substrate and at least two nanowires. Each of the at least two nanowires has a first end and a second end, the first end being attached to the substrate and the second end including a SERS-active tip. The SERS-active structure includes a ligand to the analyte molecule attached to the SERS-active structure for holding the analyte molecule in proximity to the SERS-active tips of the at least two nanowires.

A method for analyzing an analyte molecule is disclosed that includes the steps of providing a SERS-active structure, placing the analyte molecule adjacent the SERS-active structure, irradiating the SERS-active structure with excitation radiation, and detecting Raman-scattered radiation. The SERS-active structure includes a substrate and at least two nanowires. Each of the at least two nanowires has a first end and a second end, the first end being attached to the substrate and the second end including a SERS-active tip. The SERS-active structure includes a ligand to the analyte molecule attached to the SERS-active structure for holding the analyte molecule in proximity to the SERS-active tips of the at least two nanowires.

A method for forming a SERS-active structure for use in a sensor for an analyte molecule is described that includes the steps of: providing a substrate; forming a fractional monolayer of catalyst material on a surface of the substrate, the catalyst material including a SERS-active material; annealing the fractional monolayer of catalyst material to promote self-assembly of at least two nanoislands of catalyst material; and exposing the at least two nanoislands of catalyst material to a gas to promote the formation of at least two nanowires of semiconductor material, the at least two nanowires of semiconductor material including a SERS-active tip at an end thereof.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

Figure 1:
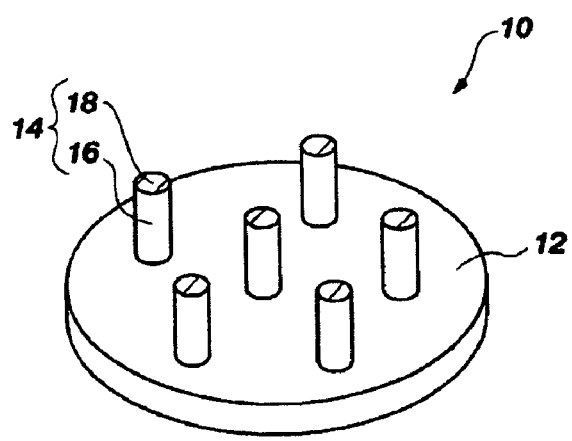
FIG. 1 is perspective view of an exemplary embodiment of a SERS-active structure according to the invention.

The present invention relates to surface enhanced Raman spectroscopy (SERS). More particularly, the invention relates to SERS-active structures for use in molecular sensors that include nanowires having SERS-active tips, methods for forming SERS-active structures, and methods for performing SERS using SERS-active structures.

The methods disclosed herein allow for the fabrication of SERS-active structures, including nanowires that extend from a surface of a substrate and have SERS-active tips. The size, location, orientation and density of the nanowires can be well controlled using the methods disclosed herein, which allows for improved enhancement of the Raman scattered signal intensity relative to previous SERS-active structures. The SERS-active structures can be functionalized to promote the attachment of analyte molecules and can be used in molecular sensors.

The term "SERS-active structure" as used herein means a structure that is capable of increasing the number of Raman photons inelastically scattered by a molecule when the molecule is located adjacent the structure, and when the molecule and structure are subjected to electromagnetic radiation.

The term "SERS-active material" as used herein means a material that, when formed into appropriate geometries or configurations, is capable of increasing the number of photons inelastically scattered by a molecule when the molecule is located adjacent the material, when the molecule and material are subjected to electromagnetic radiation, and which can be used to form a SERS-active structure.

The term "nanowire" as used herein means an elongated structure having cross-sectional dimensions of less than about 100 nanometers.

The term "crystal" as used herein means a three-dimensional structure made up of atoms or ions arranged in basic units that are repeated throughout the structure.

The term "analyte molecule" as used herein means a molecule upon which it is desired to perform SERS.

The term "equivalent monolayer" as used herein means the amount of material that would form a layer of material one atom thick if the material were uniformly distributed over an underlying surface.

The term "fractional monolayer" as used herein means the structure formed by a number of atoms or molecules when the atoms or molecules are deposited on a surface, the number of atoms or molecules being insufficient to form a monolayer that completely covers the surface.

The term "ligand" as used herein means one or more ions, molecules, or groups of molecules capable of attaching both to a SERS-active structure and to an analyte molecule to hold the analyte molecule in proximity to the SERS-active structure.

Silicon and germanium nanowires can be formed on a substrate, such as a silicon wafer, as described in T. I. Kamins, X. Li, R. Stanley Williams, and X. Liu, Nano Letters 4, 503 (2004), and in T. I. Kamins, R. Stanley Williams, T. Hesjedal, J. S. Harris, Physica E 13, 995-998 (2002), both of which are incorporated by reference herein in their entirety.

It should be understood that the illustrations presented herein are not meant to be actual views of any particular SERS-active structure, but are merely idealized representations which are employed to describe the present invention. Additionally, elements common between figures retain the same numerical designation.

An exemplary SERS-active structure 10 embodying the present invention is shown in FIG. 1. The SERS-active structure 10 includes a substrate 12 and at least two nanowires 14 disposed on the substrate 12. Each of the at least two nanowires 14 includes an elongated member 16 and a SERS-active tip 18. A first end of each nanowire 14 is attached to the substrate 12 and the SERS-active tip 18 is disposed at the opposite, second end. In this configuration, each of the at least two nanowires 14 may extend from a surface of the substrate 12. For simplicity in illustration, the SERS-active structure 10 is shown to include six nanowires 14 extending from the surface of the substrate 12. In actuality, any number (e.g., hundreds, thousands, and even millions) of nanowires 14 may extend from the surface of the substrate 12. In addition, while each nanowire 14 is shown to extend from a surface of the substrate 12 in a direction substantially perpendicular thereto, some of the nanowires 14 may extend from a surface of the substrate 12 in directions that are not perpendicular relative to the substrate 12. Each nanowire 14 may be substantially cylindrical and may have a diameter, for example, of about 5 nanometers. It is also understood that the SERS signal is proportional to the fourth power of the local electric field E, which is proportional to the inverse square of the tip diameter. Thus, as the diameter of the nanowire is reduced, the effect becomes larger. In a particular embodiment, each nanowire 14 may have a diameter of less than 5 nanometers.

Exemplary materials that may be used to form the substrate 12 include, but are not limited to, silicon, silica, germanium, II-V or II-VI semiconductor materials, metals, ceramics, and polymers. The elongated member 16 of the at least two nanowires 14 may be formed from, for example, silicon or germanium, and may consist of a single crystal. The SERS-active tip 18 of the at least two nanowires 14 may include any SERS-active material such as, for example, gold.

An exemplary method for making the SERS-active structure 10 can be described with reference to FIGS. 2A-2E. A fractional monolayer of catalyst material 20 may be deposited onto a surface of the substrate 12 to produce the structure shown schematically in FIG. 2A. For example, the fractional monolayer of catalyst material 20 may be formed from gold and substrate 12 may be an (001)-oriented silicon wafer. To deposit the fractional monolayer of gold on the silicon wafer, commercially available gold nanoparticles in aqueous suspension may be dispersed on the surface of the substrate 12 and dried. Alternatively, several equivalent monolayers of catalyst material 20 may be deposited. When depositing more than a fractional monolayer of catalyst material, it is understood that the layer of deposited catalyst material may or may not entirely cover the substrate 12 and may or may not be continuous immediately after deposition. However, during an annealing process described below, the catalyst material can form small islands having substantial thickness, thus uncovering a portion of the substrate 12. In a particular embodiment, gold may be sputtered or deposited through physical or chemical vapor deposition onto the surface of the substrate 12.

Figure 2A:
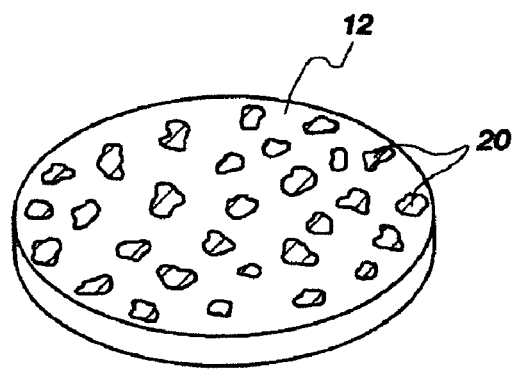
FIGS. 2A-2E illustrate an exemplary method for forming the SERS-active structure of FIG. 1.

The structure of FIG. 2A may then be annealed for approximately ten minutes at an elevated temperature such as, for example, approximately 650° C. At this elevated temperature, gold atoms from the fractional monolayer of catalyst material 20 coalesce and form self-assembled, larger nanoislands of catalyst material 22 on the surface of substrate 12 to produce the structure shown in FIG. 2B. In addition, annealing may allow the gold atoms to form particular orientations relative to the crystal structure of the underlying silicon substrate 12. FIG. 2C is a cross-sectional view of the structure of FIG. 2B taken along section line 2C-2C therein. Other annealing times and temperatures may also be used to produce the desired effects described herein without departing from the scope of the invention.

Figure 2B:
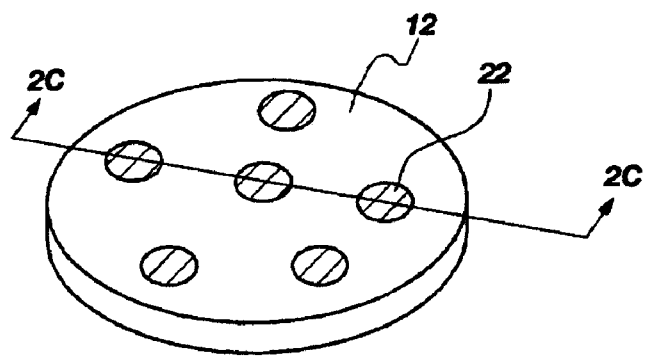
Figure 2C:
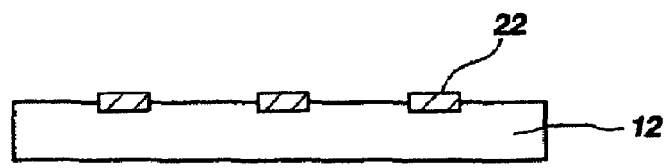
Figure 2D:
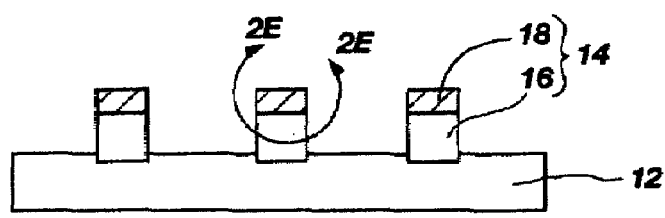

The nanowires 14 may then be formed on the surface of the substrate 12 by exposing the structure of FIGS. 2B-2C to a reactant gas containing a semiconductor element such as germanium or silicon, the decomposition of which is promoted or catalyzed by the nanoislands of catalyst material 22. Exemplary gases include, but are not limited to, $SiH_4$, $SiH_2Cl_2$, and $GeH_4$. For example, nanowires 14 that include an elongated element 16 formed from germanium may be formed by exposing the structure of FIGS. 2B-2C to $GeH_4$ at a temperature of between about 300° C. and about 400° C., such as, for example, 320° C. FIG. 2D illustrates growing elongated elements 16 of the nanowires 14. As seen therein, the nanoislands of catalyst material 22 form the SERS-active tips 18 of nanowires 14 as the elongated elements 16 grow thereunder. Therefore, the catalyst material must also be a SERS-active material. Other materials that might serve as catalyst material include titanium, silver, copper, platinum, palladium, and aluminum.

Figure 2E:
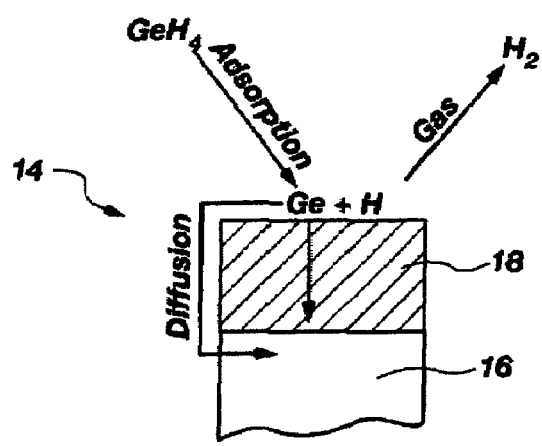

FIG. 2E is an enlarged view of the SERS-active tip 18 of one of the nanowires 14 illustrated in FIG. 2D. FIG. 2E illustrates what is believed to be the mechanism of growth of the elongated elements 16. $GeH_4$ gas adsorbs on a surface of the SERS-active tip 18, which includes catalyst material. The catalyst material causes the gas to decompose into germanium atoms and hydrogen atoms. The hydrogen atoms form hydrogen gas $H_2$, which is released from the surface of the SERS-active tip 18 to the surroundings. The germanium atoms diffuse either along the surface of the SERS-active tip 18, or through the bulk of the SERS-active tip 18, to the underlying elongated element 16. These germanium atoms are added to the growing elongated element 16. The growth of the elongated element 16 pushes the SERS-active tip 18 up and away from the surface of substrate 12, eventually forming the nanowires 14 and the SERS-active structure 10 shown in FIG. 1.

Figure 3:
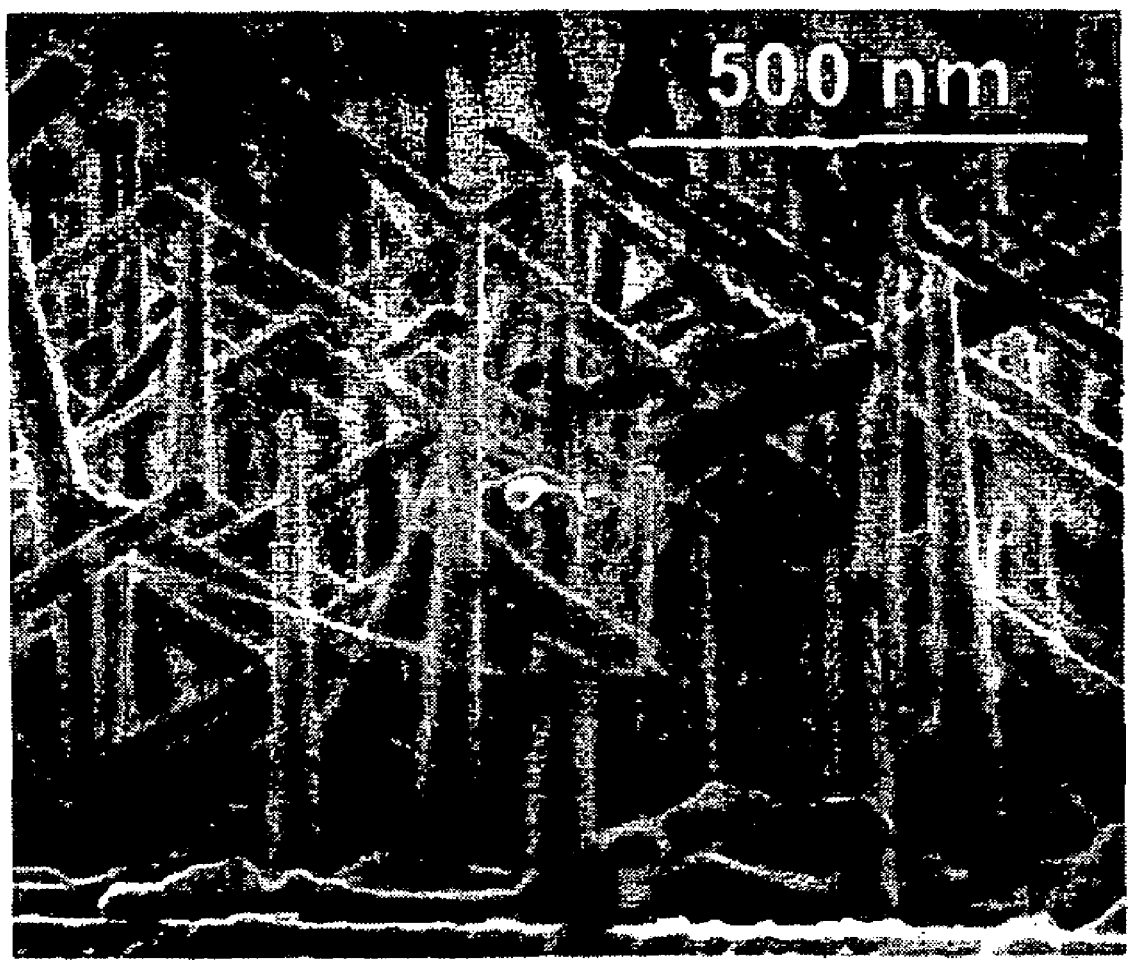
FIG. 3 is a side-view image generated by a scanning electron microscope of a SERS-active structure according to the invention that includes nanowires formed by exemplary methods disclosed herein.

FIG. 3 is a side-view image generated by a scanning electron microscope of a SERS-active structure including nanowires that were formed by the methods described herein. The nanowires of FIG. 3 include an elongated element formed from germanium and have a SERS-active tip. If a (001) oriented silicon substrate 12 is used, the nanowires may extend from a surface of the substrate 12 predominantly in the <111> equivalent directions of the silicon substrate 12. If the substrate 12 is formed from noncrystalline material, the nanowires may extend from a surface of the substrate 12 in a random direction relative to one another. In this configuration, the distances separating one SERS-active tip from neighboring or adjacent SERS-active tips may be very different from the distances separating another SERS-active tip from neighboring or adjacent SERS-active tips. Thus, a wide range of relative distances can be produced.

After randomly oriented nanowires have been formed on a substrate, they can be substantially aligned such that they extend from a surface of the substrate in substantially the same predetermined direction by exposing the nanowires to a flux of energetic ions such as, for example, argon ions having an ion energy of 5 KV and an ion current of 1 μA as described in U.S. Pat. No. 6,248,674 to Kamins et al., the contents of which are incorporated by reference herein. After ion bombardment, the distances separating SERS-active tips from neighboring or adjacent SERS-active tips may be more uniform.

Figure 4:
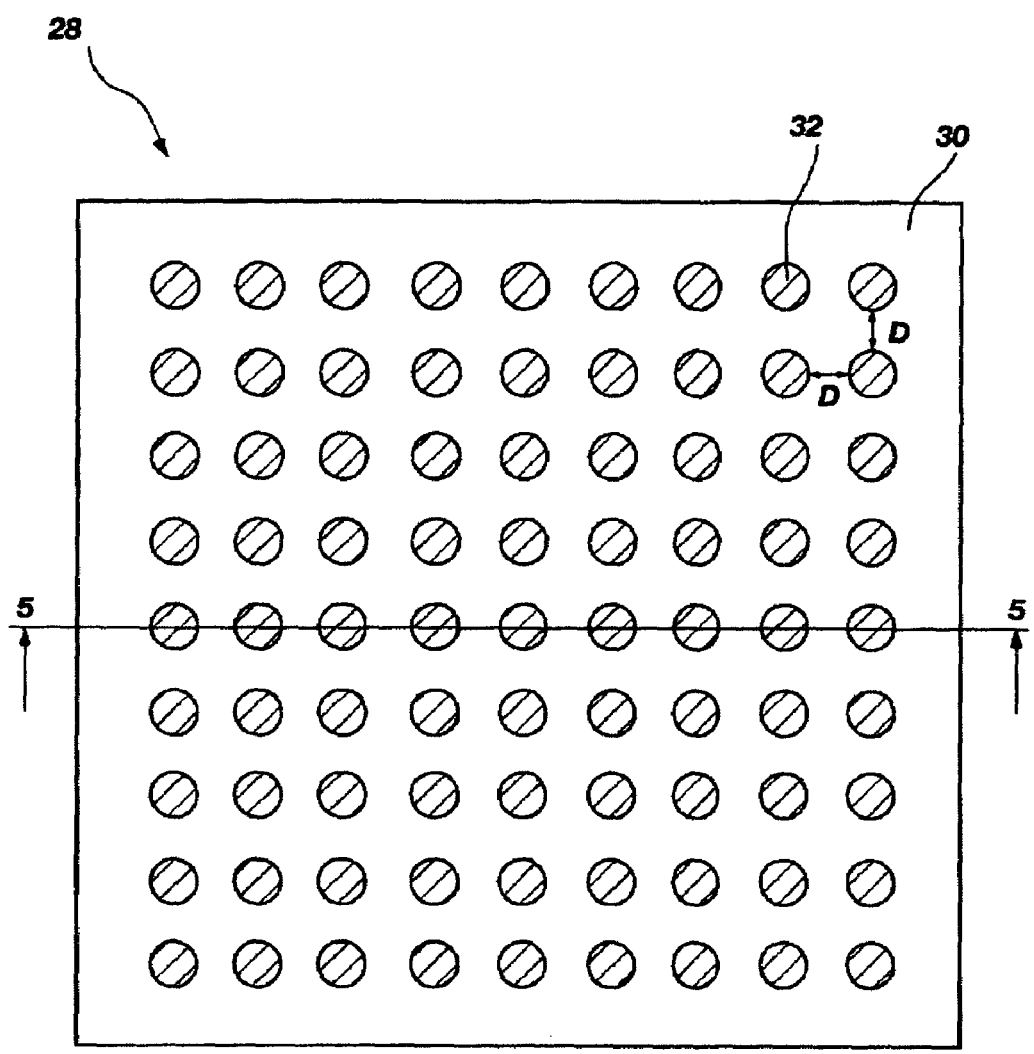
FIG. 4 is top plan view of an exemplary embodiment of a SERS-active structure according to the invention.
Figure 5:
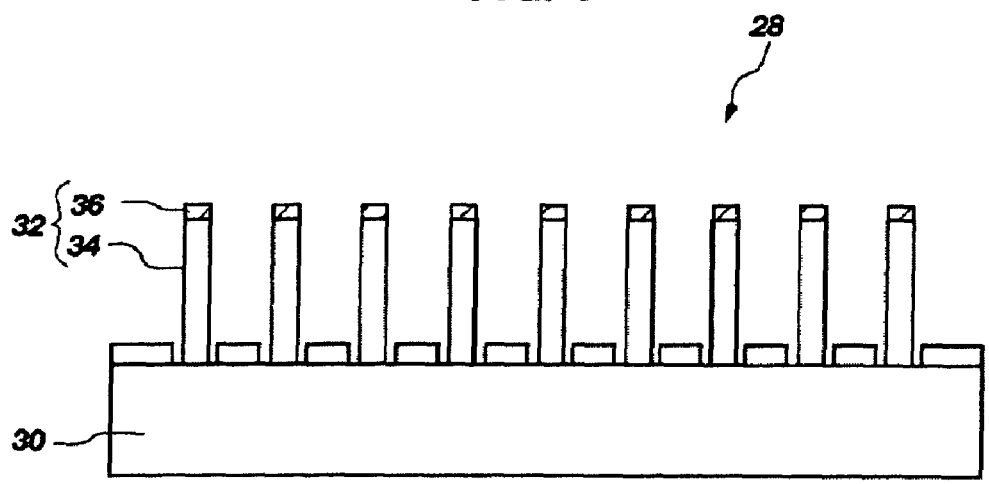
FIG. 5 is a cross-sectional view of the SERS-active structure of FIG. 4 taken along section line 5-5 therein.

Another exemplary SERS-active structure 28 embodying the present invention is shown schematically in FIGS. 4-5. The SERS-active structure 28 includes a substrate 30 and a plurality of nanowires 32 disposed on a surface of the substrate 30. As seen in FIG. 5, each nanowire 32 of the plurality of nanowires includes an elongated member 34 and a SERS-active tip 36. A first end of each nanowire 32 is attached to the substrate 30 and disposed thereon at a predetermined location. The SERS-active tip 36 is disposed at the opposite, second end of each nanowire 32. In this configuration, each nanowire 32 may extend from a surface of the substrate 30.

For simplicity in illustration, the SERS-active structure 28 is shown to include an array of eighty-one nanowires 32 extending from the surface of the substrate 30. In actuality, any number (e.g., hundreds, thousands, and even millions) of nanowires 32 may extend from the surface of the substrate 30. In addition, while each nanowire 32 is shown to extend from a surface of the substrate 30 in a direction substantially perpendicular thereto, some of the nanowires 32 may extend from a surface of the substrate 30 in directions that are not perpendicular relative to the substrate 30. Each nanowire 32 may be substantially cylindrical and have a diameter of at least about 5 nanometers.

Substrate 30 may include, for example, a (111)-oriented silicon wafer. The elongated member 34 and the SERS-active tip 36 of SERS-active structure 28 may be formed from materials identical to those discussed previously in relation to the SERS-active structure 10 of FIG. 1.

As seen in FIG. 4, each nanowire 32 of the plurality is disposed at a predetermined location on the surface of the substrate 30 and is separated from adjacent nanowires by a predetermined distance D. The predetermined distance D is at least about 1 nanometer. This allows the SERS-active structure 28 to have a predetermined density of nanowires 32 on the surface of the substrate 30. In other words, the number of nanowires 32 per unit area on the surface of the substrate 30 may be well controlled.

The predetermined distance D may be selected to correspond to the size of a particular analyte molecule to be analyzed with the SERS-active structure 28, such that the molecule is capable of draping or extending substantially between two adjacent nanowires 32. Molecules positioned between two nanoparticles of SERS-active material are believed to significantly enhance the Raman signal emitted by an analyte molecule.

Figure 6A:
FIGS. 6A-6F illustrate an exemplary method for forming the SERS-active structure of FIGS. 4-5.
Figure 6B:
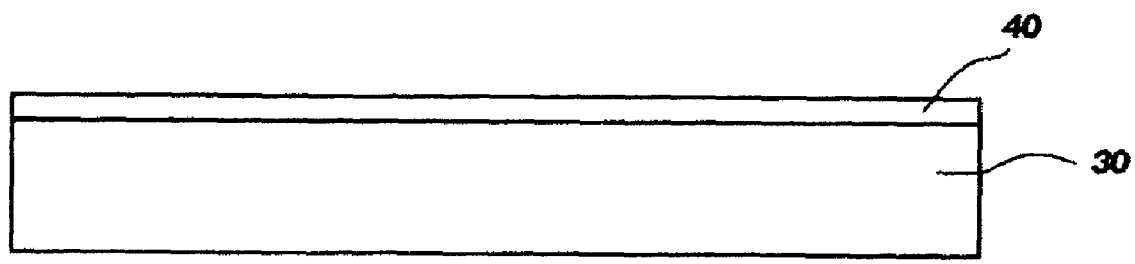

An exemplary method for making the SERS-active structure 28 can be described with reference to FIGS. 6A-6F. To make the SERS-active structure 28, a substrate 30 may be provided as shown in FIG. 6A. The substrate 30 may include, for example, a (111)-oriented silicon wafer or die. Next, an oxide layer 40 may be formed on or in the surface of the substrate 30, as shown in FIG. 6B. Various methods for forming an oxide layer on or in a surface of a substrate are known in the art of microdevice fabrication, any of which can be used to form the oxide layer 40.

Figure 6C:
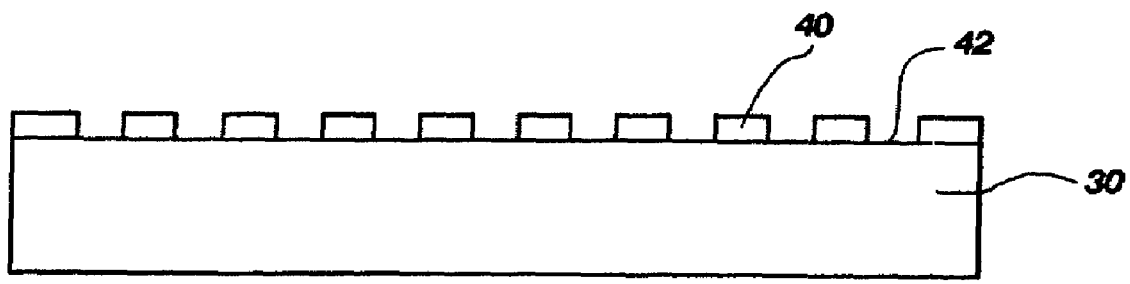

A portion or portions of the oxide layer 40 may be lithographically removed to form regions of exposed silicon material 42 of the underlying substrate 30, as shown in FIG. 6C. For example, the oxide layer 40 may be masked and etched as known in the art of microdevice fabrication to remove portions thereof. Each region of exposed silicon material 42 may be disposed at predetermined locations where the nanowires 32 are to be formed.

Figure 6D:
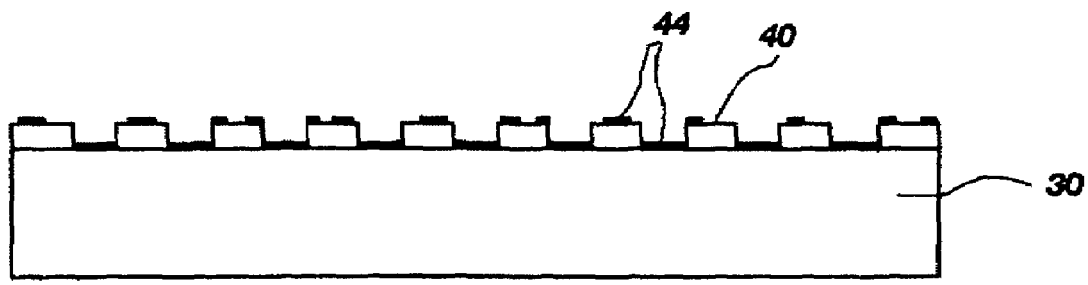

A fractional monolayer of catalyst material 44 may then be formed or deposited on a surface of the device over the oxide layer 40 and regions of exposed silicon material 42, as shown in FIG. 6D. For example, a fractional monolayer 44 including gold may be deposited by chemical or physical vapor deposition of gold, or by dispersing gold nanoparticles in an aqueous solution over the structure to form the structure shown in FIG. 6D. Any gold disposed on the oxide layer 40 may be removed by, for example, chemical-mechanical polishing or, alternatively, may be moved from $SiO_2$ to exposed Si regions through diffusion.

Figure 6E:
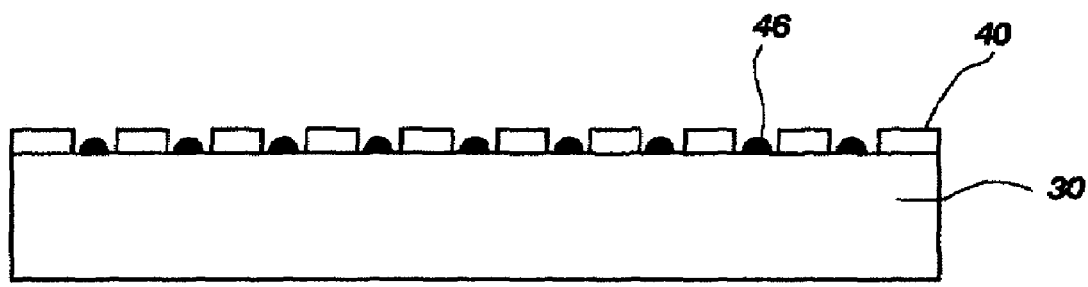

One or more nanoislands 46 of catalyst material may be formed at each region of exposed silicon material 42, as shown in FIG. 6E, by annealing the device for approximately ten minutes at an elevated temperature such as, for example, approximately 650° C. Generally, the temperature used will depend on the catalyst material. The size, shape, and number of the nanoislands 46 may be modified by varying the temperature and duration of the annealing process. For example, a large number of small nanoislands may be present after deposition. Many of the small nanoislands can be coalesced into a smaller number of larger nanoislands upon annealing.

Figure 6F:
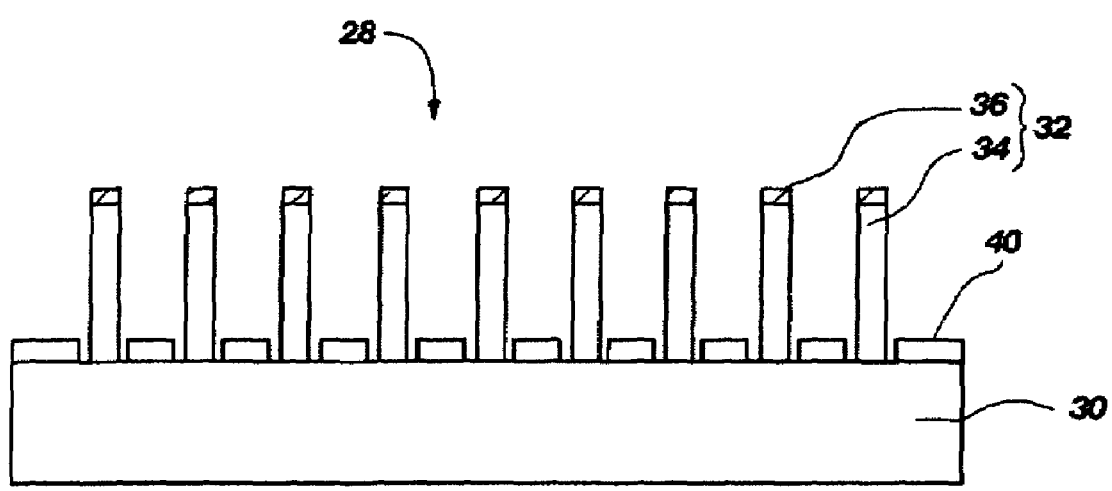

After the nanoislands 46 of catalyst material have formed at the predetermined locations on the regions of exposed silicon material 42, elongated members 34 formed from germanium may be grown by exposing the device to $GeH_4$ gas at temperatures between about 300° C. and about 400° C. The gold-containing catalyst material causes the germanium-containing gas to decompose and the elongated members 34 of germanium material to grow in one dimension, forming the nanowires 32, as shown in FIG. 6F. The length of the growing nanowires 32 may correspond to the duration of the reaction process. The mechanism of growth of the elongated members 34 is substantially identical to the mechanism described previously in relation to FIG. 2E.

Figure 7A:
FIGS. 7A-7G illustrate an exemplary method for forming the SERS-active structure of FIGS. 4-5.
Figure 7B:
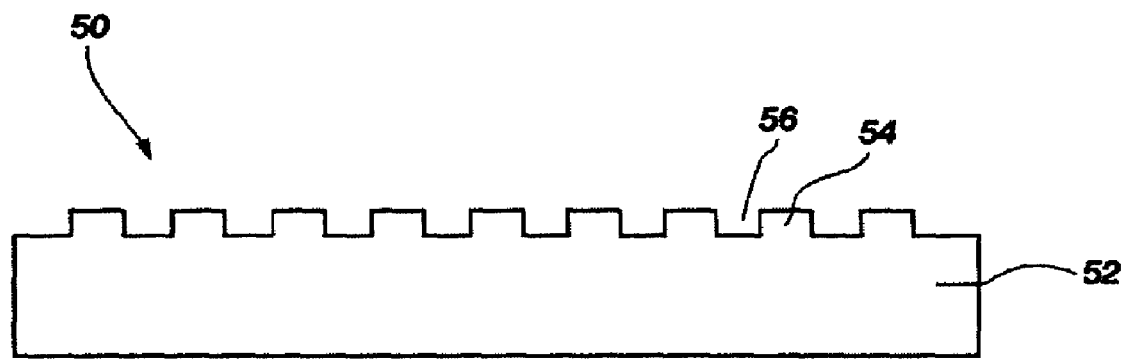

An alternative imprinting method for forming the SERS-active structure 28 can be described with reference to FIGS. 7A-7G. Referring to FIGS. 7A-7B, a mold 50 may be formed from a mold substrate 52. The mold substrate 52 may be made from, for example, silicon, other semiconductor materials, ceramics, plastics, metals, or any other suitable material. A plurality of protrusions 54 and recesses 56 (FIG. 7B) may be formed in a surface of the mold substrate 52 to form the mold 50 using electron beam lithography and reactive ion etching, or any other appropriate method known in the art of microdevice fabrication. The size, shape, and location of the protrusions 54 may be substantially identical to the predetermined cross-sectional size, shape, and location of the nanowires 32 to be formed on the surface of the substrate 30. Alternatively, nano-printing may also be performed by, for example, providing catalyst material on a mold and transferring the catalyst material to a substrate for subsequent use as nucleation centers for growing nanowires.

Figure 7C:
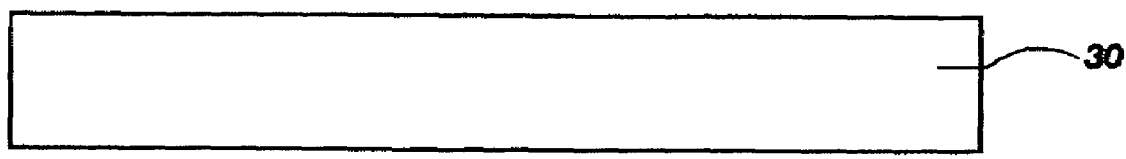
Figure 7D:
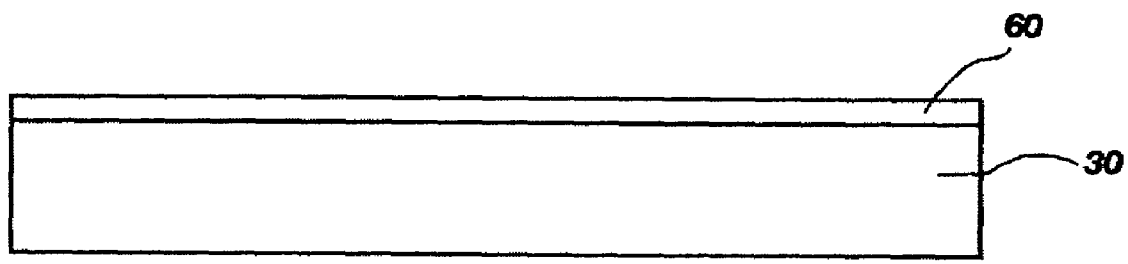

Referring to FIG. 7C, a SERS-active structure substrate 30 may be provided, and a layer of deformable material 60 may be applied to a surface thereof to form the structure shown in FIG. 7D. The layer of deformable material 60 may include a thermoplastic polymer such as, for example, poly(methyl methacrylate) (PMMA). In a representative example, the thickness of the layer of deformable material 60 may be between about 1 and about 200 nanometers.

Figure 7E:
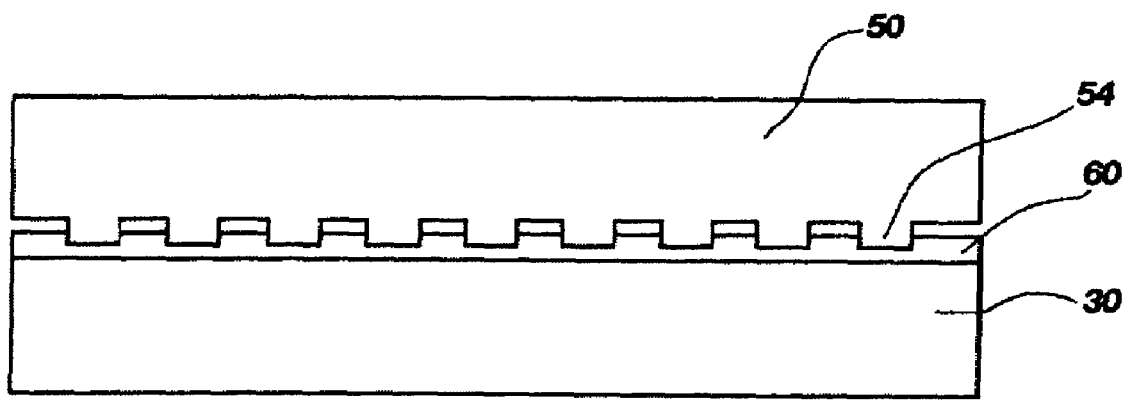
Figure 7F:
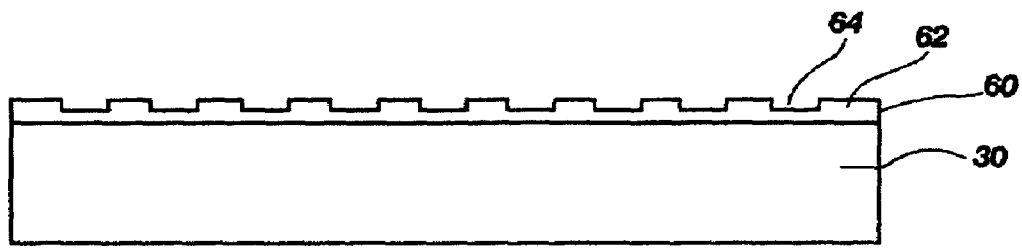

The mold 50 may be pressed against the SERS-active structure substrate 30 as shown in FIG. 7E such that the protrusions 54 of the mold 50 are pressed into the layer of deformable material 60. The protrusions 54 and recesses 56 of the mold 50 form a pattern of corresponding and complementary recesses 64 and protrusions 62 in the layer of deformable material 60, forming the structure shown in FIG. 7F. The layer of deformable material 60 may be softened by heating the deformable material 60 to a temperature above the glass transition temperature thereof prior to pressing the mold 50 against the SERS-active structure substrate 30. The mold 50 may be removed subsequent to cooling the layer of deformable material 60 to a temperature below the glass transition temperature of the material.

Figure 7G:
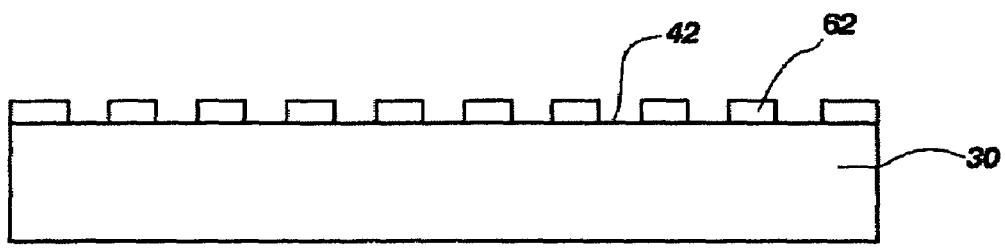

A portion of the patterned layer of deformable material 60 may be removed by uniformly etching the patterned layer of deformable material 60 until regions of exposed silicon material 42 of the underlying SERS-active structure substrate 30 are exposed, as shown in FIG. 7G. As seen therein, only a portion of the protrusions 62 of the layer of deformable material 60 may remain, and the underlying SERS-active structure substrate 30 may be exposed at the regions where the recesses 64 were previously located.

The structure of FIG. 7G is substantially similar to the structure of FIG. 6C and includes exposed regions of silicon material 42 disposed at predetermined locations on the surface of the substrate 30. The structure of FIG. 7G includes protrusions 62 of a patterned layer of deformable material 60, while the structure of FIG. 6C includes a patterned oxide layer 40. The SERS-active structure 28 may be formed from the structure of FIG. 7G in substantially the same manner as it is formed from the structure of FIG. 6C, as described previously herein. However, after depositing the SERS-active material over the structure shown in FIG. 7G, the remaining protrusions 62 of the layer of deformable material 60 may be removed prior to growing the nanowires at elevated temperatures as the deformable material might decompose at the elevated temperatures or might hinder the catalysis of the decomposition reaction.

Figure 8:
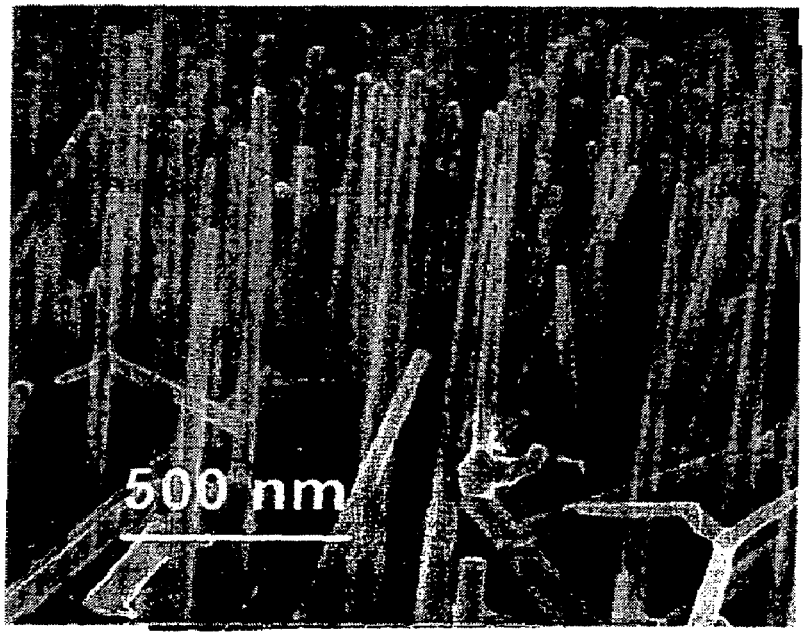
FIG. 8 is a side-view image generated by a scanning electron microscope of a SERS-active structure according to the invention that includes substantially aligned nanowires formed by exemplary methods disclosed herein.

FIG. 8 is a side-view image generated by a scanning electron microscope of an additional SERS-active structure that includes nanowires formed from germanium. The nanowires have a SERS-active tip and extend substantially perpendicular relative to the surface of the substrate and in a direction substantially parallel to adjacent nanowires. As can be seen in the images of FIGS. 3 and 8, the SERS-active structures described herein have high ratios of surface area to volume, which is ideal for a SERS analyte substrate.

The SERS active structures 10, 28 described herein may also be coated with SERS-active materials including, but not limited to, gold, silver, and copper prior to being used as an analyte substrate. The coating may cover the entire structure, including the nanowires 14, 32 and the substrate 12, 30, or any part thereof. Such a coating may increase the number of localized "hot spots" on the SERS-active structure at which the surface enhancement effect is observed, thereby making the structure more efficient in enhancing the Raman signal relative to un-coated structures.

To use a SERS-active structure that embodies the present invention (such as SERS-active structures 10 and 28) in a molecular sensor, the SERS-active structure may be derivatized or functionalized by attachment of receptors or ligands that promote the binding of a particular analyte molecule in close proximity to the SERS-active tips. The ligand may be repulsive or neutral relative to other molecules. The ligand and the analyte molecule may consist of what is often referred to as a specific pair or a recognition pair of molecules. The particular analyte molecule may include, but is not limited to, biomolecules such as nucleic acids, proteins, hormones, sugars, and metabolites. The ligand may include, but is not limited to, antibodies, receptors, and nucleic acids. Techniques for functionalizing surfaces for attachment of particular analyte molecules thereto have been researched and developed extensively in the art of biosensors and bioassays and can be employed in the present invention.

Figure 9:
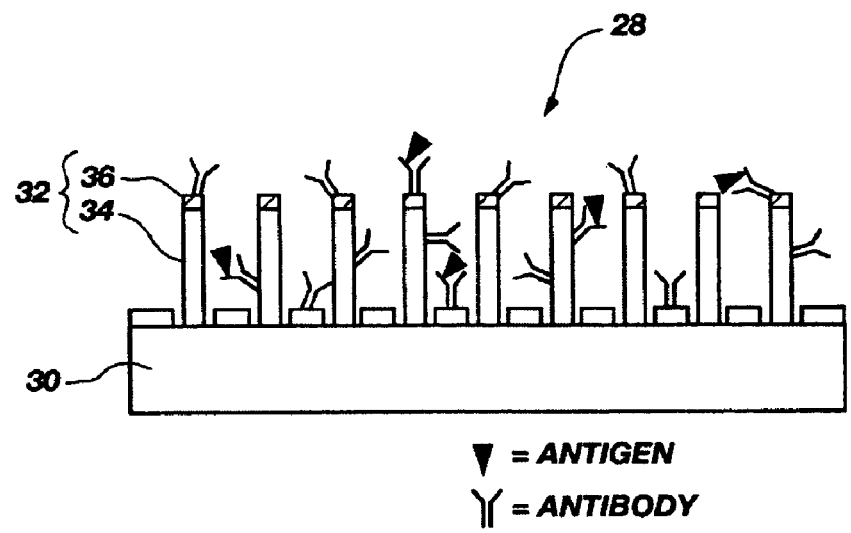
FIG. 9 is a cross-sectional view of the SERS-active structures of FIGS. 4 and 5 illustrating the use of antibodies to promote binding of an antigen analyte molecule to the SERS-active structure.

FIG. 9 illustrates an exemplary SERS-active structure 28 configured for use in a molecular sensor. Representative antibodies are attached to the SERS-active structure 28 and, in turn, bind to a particular representative antigen that is desired to be detected and analyzed. The ligand antibodies may be attached to any part of the SERS-active structure 28, including the substrate 30 and the nanowires 32. In the presence of the antigen, the antibodies will bind to the antigens and hold them in close proximity to the SERS-active tips 36 as shown in FIG. 9, allowing the antigens to be detected and analyzed by SERS.

If the ligand antibodies are not directly attachable to the SERS-active structure 28, other molecules may be used to attach the antibodies to the SERS-active structure 28. For example, organic molecules of the general formula X-R-Y may be used, wherein X is a functional group that will bind to a feature or surface of the SERS-active structure 28 and Y is a functional group that will bind to the desired ligand. Exemplary functional groups for Y include, but are not limited to, a hydroxyl, carboxyl, amino, aldehyde, hydrazide, carbonyl, epoxy, or vinyl group. R may be a hydrocarbon chain or any other suitable chemical structure.

The SERS-active tips 36 of SERS-active structure 28 may include gold. Therefore, for example, X may include functional groups known to bind to gold such as, for example, asymmetrical or symmetrical disulfide, sulfide, diselenide, selenide, thiol, nitrile, isonitrile, nitro, selenol, trivalent phosphorus compounds, isothiocyanate, xanthate, thiocarbamate, phosphine, thioacid or dithioacid. Other functional groups are known to bind to silicon, germanium, and oxides thereof, and may be used to bind the ligand to other features of the SERS-active structure 28 such as elongated member 34 and substrate 30.

If the particular ligands are difficult to bind to the SERS-active structure, material to which the ligands are easily bound may be deposited on the SERS-active structure 28 as long as the material does not interfere with the surface enhancement of Raman scattering effected by the SERS-active tips. For example, a thin layer of gold may be applied over the entire SERS-active structure 28 prior to attachment of ligands thereto. Gold is a known SERS-active material and therefore will not interfere with the surface enhancement of Raman scattering, and may in fact further enhance the phenomenon. After depositing the thin layer of gold, the ligands may be attached thereto as described above.

Figure 10:
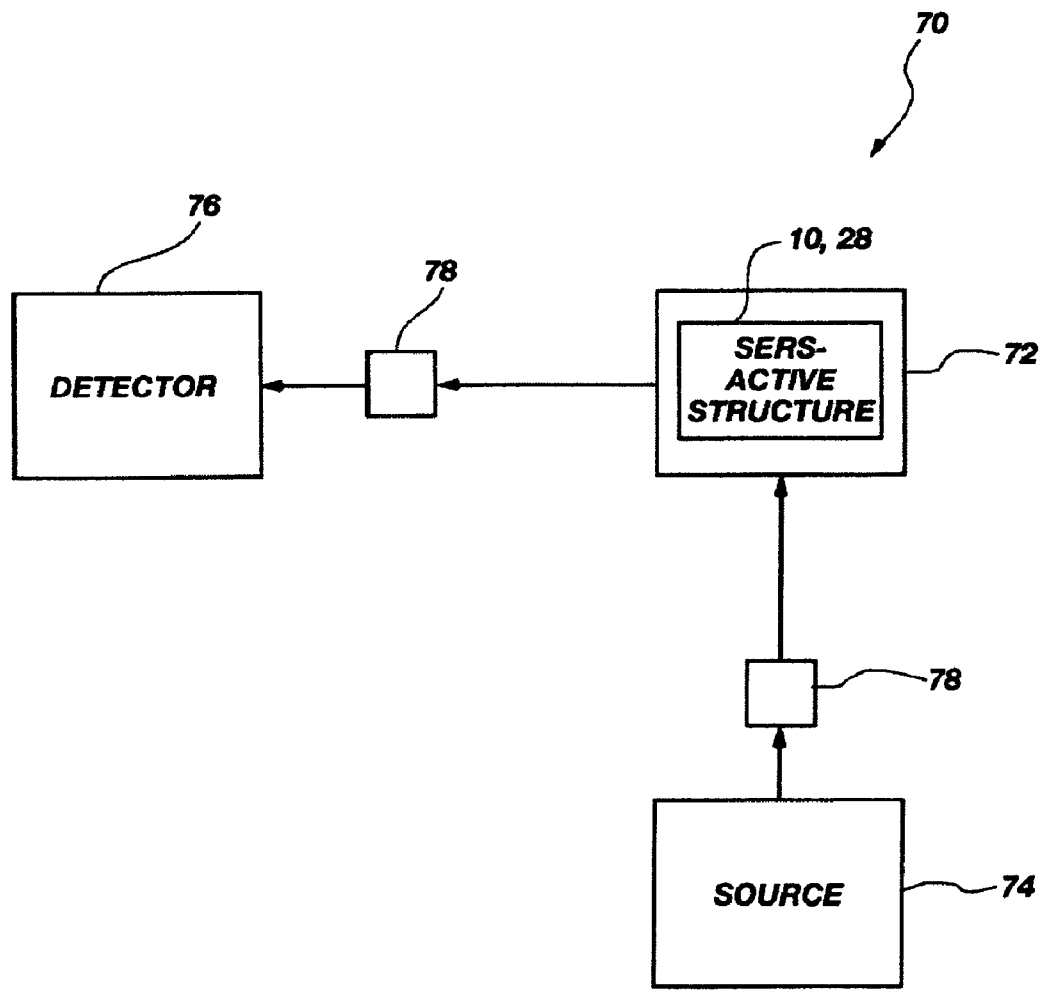
FIG. 10 is a schematic diagram of an exemplary SERS system for performing surface enhanced Raman spectroscopy using a SERS-active structure according to the invention.

An exemplary SERS system 70 that can operate as a molecular sensor according to the invention is illustrated schematically in FIG. 10. The system 70 may include one of the exemplary SERS-active structures 10 and 28 described herein, and may be used to perform surface enhanced Raman spectroscopy. The SERS system 70 may include a sample or analyte stage 72, an excitation radiation source 74, and a detector 76. The analyte stage 72 may be formed as a probe customized for testing a particular environment. The analyte stage 72 may include either the SERS-active structure 10 or the SERS-active structure 28. The SERS system 70 also may include various optical components 78 such as, for example, lenses and filters positioned between the excitation radiation source 74 and the analyte stage 72 and between the analyte stage 72 and the detector 76.

The excitation radiation source 74 may include any suitable source for emitting radiation at the desired wavelength, and may be capable of emitting a tunable wavelength of radiation. For example, commercially available semiconductor lasers, helium-neon lasers, carbon dioxide lasers, light emitting diodes, incandescent lamps, and many other known radiation emitting sources may be used as the excitation radiation source 74. The wavelengths that are emitted by the excitation radiation source 74 may be any suitable wavelength for properly analyzing the analyte using SERS. An exemplary range of wavelengths that may be emitted by the excitation radiation source 74 includes wavelengths between about 350 nm and about 1000 nm.

The excitation radiation emitted by the source 74 may be delivered directly from the source 74 to the analyte stage 72 and the SERS-active structure 10,28. Alternatively, collimation, filtration, and subsequent focusing of the excitation radiation may be performed by optical components 78 before the excitation radiation impinges on the analyte stage 72 and the SERS-active structure 10, 28. The excitation radiation may be transferred to the SERS-active structure 10, 28 from the source 74, and Raman radiation may be transferred to the detector 76 from the SERS-active structure 10, 28, using optical fibers. Alternatively, the radiation may travel directly through space in a vacuum.

The SERS-active structure 10, 28 of the analyte stage 72 enhances the Raman signal of the analyte molecules, as previously discussed. When the excitation radiation impinges on the structure, the SERS active regions strongly increase the number of photons inelastically scattered by an analyte molecule positioned near or adjacent to the SERS-active structure 10, 28.

The Raman scattered photons may be collimated, filtered, or focused with optical components 78 positioned between the analyte stage 72 and the detector 76. For example, a filter or a plurality of filters may be employed, either as part of the structure of the detector 76, or as a separate unit that is configured to filter the wavelength of the excitation radiation, thus allowing only the Raman scattered photons to be received by the detector 76.

The detector 76 receives and detects the Raman scattered photons and may include a monochromator (or any other suitable device for determining the wavelength of the Raman scattered photons) and a device such as, for example, a photomultiplier for determining the quantity of Raman scattered photons (intensity).

Typically, the Raman scattered photons are scattered isotropically (i.e., being scattered in all directions) relative to the analyte stage 72. Thus, the position of the detector 76 relative to the analyte stage 72 is not particularly important. However, the detector 76 may be positioned at, for example, an angle of 90° relative to the direction of the incident excitation radiation to minimize the intensity of the incident excitation radiation that may be incident on the detector 76, as shown in FIG. 10.

To perform SERS using the system 70, a user may functionalize or derivatize a surface of the SERS-active structure 10, 28 as described herein. The SERS-active structure 10, 28 can then be placed in an environment in which a particular analyte molecule is desired to be detected and analyzed. The SERS-active structure 10, 28 is then irradiated with excitation radiation or light from the source 74. Raman scattered photons scattered by any molecules present are detected by the detector 76. The wavelength and intensity of the photons can be determined, which can be used to identify and provide information about the molecules present.

The structures and systems disclosed herein may also be used to perform hyper-Raman spectroscopy. When excitation radiation impinges on an analyte molecule, a very small number of photons may be scattered at frequencies corresponding to the higher order harmonics of the excitation radiation, such as the second and third harmonics (i.e., twice or three times the frequency of the excitation radiation). Some of these photons may have a frequency that is Raman-shifted relative to the frequencies corresponding to the higher order harmonics of the excitation radiation. These higher order Raman-scattered photons can provide information about the analyte molecule that cannot be obtained by first order Raman spectroscopy. Hyper-Raman spectroscopy involves the collection and analysis of these higher order Raman-scattered photons.

The methods disclosed herein allow for the reproducible formation of SERS-active structures that include nanowires having SERS-active tips, the nanowires having well controlled size, location, orientation, and density. These structures allow for improved surface-enhanced Raman spectroscopy and may be employed as molecular sensors having superior sensitivity relative to conventional SERS-active structures. The performance of nanoscale electronics, optoelectronics, molecular sensors, and other devices employing the Raman effect may be significantly improved by using the SERS-active structures disclosed herein.

The SERS-active structures disclosed herein may be employed in conventional table-top SERS systems in which analyte molecules are placed adjacent to the SERS-active structure and analyzed. Alternatively, the SERS-active structures may be incorporated into smaller, portable molecular sensor SERS systems, such as, for example, systems having SERS-active structures that include a sensing probe. In a particular embodiment, the probe and SERS-active structure could be placed in an environment in which it is desired to detect analyte molecules. Such a SERS system could be used, for example, by physicians for detection of molecules in the body or by an environmental scientist for detection of environmental contaminants.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A SERS-active structure for use in a sensor for an analyte molecule comprising:
a substrate;
at least two nanowires, each of the at least two nanowires being comprised of a first material and having a first end and a second end, the first end being attached to the substrate and the second end including a SERS-active tip comprising a catalytic material differing from the first material; and
an analyte molecule ligand attached to the SERS-active structure for holding the analyte molecule in proximity to the SERS-active tips of the at least two nanowires.

2. The SERS-active structure of claim 1, wherein the first material comprises a semiconductor material.

3. The SERS-active structure of claim 2, wherein the semiconductor material comprises silicon or germanium.

4. The SERS-active structure of claim 3, wherein the semiconductor material is formed as a single crystal.

5. The SERS-active structure of claim 1, wherein the catalytic material comprises a metal.

6. The SERS-active structure of claim 5, wherein the metal comprises gold.

7. The SERS-active structure of claim 1, wherein each of the at least two nanowires are substantially cylindrical and have a diameter of up to about 5 nanometers.

8. The SERS-active structure of claim 1, wherein the at least two nanowires comprises a plurality of nanowires.

9. The SERS-active structure of claim 8, wherein the first end of each nanowire of the plurality of nanowires is disposed on a surface of the substrate at a predetermined location.

10. The SERS-active structure of claim 8, wherein the first end of each nanowire of the plurality of nanowires is disposed on a surface of the substrate in a predetermined density.

11. The SERS-active structure of claim 8, wherein each nanowire of the plurality of nanowires extends from a surface of the substrate in a random direction.

12. The SERS-active structure of claim 8, wherein each nanowire of the plurality of nanowires extends from a surface of the substrate in a predetermined direction.

13. The SERS-active structure of claim 12, wherein the predetermined direction is substantially perpendicular to a surface of the substrate.

14. The SERS-active structure of claim 8, wherein each SERS-active tip of each nanowire of the plurality of nanowires is separated from adjacent SERS-active tips by a distance of between about 1 and about 50 nanometers.

15. The SERS-active structure of claim 14, wherein each nanowire of the plurality of nanowires is separated from adjacent nanowires by a distance of between about 1 and about 10 nanometers.

16. The SERS-active structure of claim 8, wherein each nanowire of the plurality of nanowires is separated from adjacent nanowires by a predetermined distance.

17. The SERS-active structure of claim 16, wherein the plurality of nanowires lie substantially parallel in relation to one another.

18. The SERS-active structure of claim 1, wherein the substrate comprises a (001)-oriented silicon substrate or a (111)-oriented silicon substrate.

19. The SERS-active structure of claim 1, further including a coating of SERS-active material on at least a portion of each of the at least two nanowires.

20. The SERS-active structure of claim 19, wherein the coating of SERS-active material comprises gold, silver, copper, platinum, palladium, titanium, or aluminum.

21. The SERS-active structure of claim 1, further including an analyte molecule attached to the ligand and disposed in proximity to the SERS-active tips of the at least two nanowires.

22. The SERS-active structure of claim 1, wherein the ligand comprises an antibody and the analyte molecule comprises an antigen to the antibody.

23. A SERS system operable as a sensor for an analyte molecule comprising:
a SERS-active structure comprising:
a substrate;
at least two nanowires, each of the at least two nanowires having a first end and a second end, the first end being attached to the substrate and the second end including a SERS-active tip comprising a catalytic material for catalyzing formation of the at least two nanowires; and
an analyte molecule ligand bound to the SERS-active structure for holding the analyte molecule in proximity to the SERS-active tips of the at least two nanowires;
an excitation radiation source configured to irradiate the SERS-active structure; and
a detector configured to receive Raman-scattered radiation scattered by an analyte molecule located adjacent the SERS-active structure.

24. The SERS system of claim 23, wherein each of the at least two nanowires comprises silicon or germanium.

25. The SERS system of claim 23, wherein the catalytic material comprises gold, silver, copper, platinum, palladium, titanium, or aluminum.

26. The SERS system of claim 23, wherein each of the at least two nanowires are substantially cylindrical and have a diameter of at least about 5 nanometers.

27. The SERS system of claim 23, wherein the at least two nanowires comprise a plurality of nanowires.

28. The SERS system of claim 27, wherein the first end of each nanowire of the plurality of nanowires is disposed on a surface of the substrate at a predetermined location.

29. The SERS system of claim 28, wherein each nanowire of the plurality of nanowires lies substantially parallel to adjacent nanowires.

30. The SERS system of claim 27, wherein each nanowire of the plurality of nanowires is separated from adjacent nanowires by a distance of between about 1 and about 50 nanometers.

31. The SERS system of claim 27, wherein each nanowire of the plurality of nanowires is separated from adjacent nanowires by a predetermined distance.

32. The SERS system of claim 23, wherein the substrate comprises an (001)-oriented silicon substrate or a (111)-oriented silicon substrate.

33. The SERS system of claim 23, further including an analyte molecule attached to the ligand and disposed in proximity to the SERS-active tips of the at least two nanowires.

34. The SERS system of claim 23, wherein the ligand comprises an antibody and the analyte molecule comprises an antigen to the antibody.

35. A method for detecting an analyte molecule comprising:
- providing a SERS-active structure comprising:
  - providing a substrate;
  - catalyzing formation of at least two nanowires on the substrate using a SERS-active catalyst material, each of the at least two nanowires having a first end and a second end, the first end being attached to the substrate and the second end including a SERS-active tip comprising the SERS-active catalyst material; and
  - attaching an analyte molecule ligand to the SERS-active structure holding the analyte molecule in proximity to the SERS-active tips of the at least two nanowires;
- placing the SERS-active structure in an environment in which it is desired to detect the analyte molecule;
- irradiating the SERS-active structure with excitation radiation; and
- detecting Raman-scattered radiation.

36. The method of claim 35, wherein the step of detecting comprises detecting Raman scatted radiation scattered by a single molecule.

37. A method for analyzing an analyte molecule comprising:
- providing a SERS-active structure comprising:
  - providing a substrate;
  - catalyzing formation of at least two nanowires on the substrate using a SERS-active catalyst material, each of the at least two nanowires having a first end and a second end, the first end being attached to the substrate and the second end including a SERS-active tip; and
  - attaching an analyte molecule ligand to the SERS-active structure for holding the analyte molecule in proximity to the SERS-active tips of the at least two nanowires;
- placing the analyte molecule adjacent the SERS-active structure;
- irradiating the SERS-active structure with excitation radiation; and
- detecting Raman-scattered radiation.

38. The method of claim 37, wherein the step of detecting comprises detecting Raman scatted radiation scattered by a single molecule.

39. A method for forming a SERS-active structure for use in a sensor for an analyte molecule comprising:
- providing a substrate;
- depositing catalyst material on a surface of the substrate, the catalyst material including a SERS-active material;
- annealing the catalyst material to promote self-assembly of at least two nanoislands of catalyst material; and
- exposing the at least two nanoislands of catalyst material to a gas to promote the formation of at least two nanowires of semiconductor material, the at least two nanowires of semiconductor material including a SERS-active tip at an end thereof.

40. The method of claim 39, wherein the SERS-active material comprises gold, silver, copper, platinum, palladium, titanium, or aluminum.

41. The method of claim 40, further comprising the step of attaching an analyte molecule ligand to the substrate or to one of the at least two nanowires.

42. The method of claim 39, wherein the gas comprises $SiH_4$, $SiH_2Cl_2$, $SiCl_4$, $Si_2H_6$, $GeH$, or $GeCl_4$.

* * * * *

UNITED STATES PATENT AND TRADEMARK OFFICE
CERTIFICATE OF CORRECTION

PATENT NO. : 7,245,370 B2  
APPLICATION NO. : 11/030733  
DATED : July 17, 2007  
INVENTOR(S) : Alexandre Bratkovski et al.

Page 1 of 1

It is certified that error appears in the above-identified patent and that said Letters Patent is hereby corrected as shown below:

In column 5, line 57, delete "II-V" and insert -- III-V --, therefor.

In column 14, line 56, in Claim 30, delete "1and" and insert -- 1 and --, therefor.

In column 15, line 16, in Claim 35, after "structure" insert -- for --.

In column 15, line 25, in Claim 36, after "Raman" delete "scatted" and insert -- scattered --, therefor.

In column 16, line 12, in Claim 38, after "Raman" delete "scatted" and insert -- scattered --, therefor.

Signed and Sealed this

Sixth Day of October, 2009

David J. Kappos  
*Director of the United States Patent and Trademark Office*